United States Patent [19]

Boell

[11] 4,022,804

[45] May 10, 1977

[54] PROCESS FOR THE PRODUCTION OF BROMO SUBSTITUTED TETRAHYDROFURAN SULFONES

[75] Inventor: Walter Boell, Mutterstadt, Germany

[73] Assignee: BASF Aktiengesellschaft, Ludwigshafen (Rhine), Germany

[22] Filed: July 16, 1975

[21] Appl. No.: 596,305

[30] Foreign Application Priority Data

July 22, 1974 Germany .......................... 2435098

[52] U.S. Cl. .......................... 260/345.1; 260/345.7; 260/515 M; 260/607 AR; 260/607 AL
[51] Int. Cl.² ...................................... C07D 309/02
[58] Field of Search .... 260/607 AR, 345.1, 515 M, 260/345.7, 607 AL

[56] References Cited

UNITED STATES PATENTS 2,573,580  10/1951  Ladd .......................... 260/607 AR

OTHER PUBLICATIONS

J. Org. Chem. vol. 39 No. 26 pp. 3867–3870 (1974).
Tet. (1965) vol. 21 pp. 2743–2747.

*Primary Examiner*—Delbert R. Phillips
*Attorney, Agent, or Firm*—Johnston, Keil, Thompson & Shurtleff

[57] ABSTRACT

A process for the manufacture of β-bromoalkylsulfones and β-bromoalkenylsulfones by addition reaction of sulfonic acid bromides with olefins or acetylenes in the presence of hydroperoxide and, optionally, of metal salts. Starting materials for further syntheses and for biologically active compounds may be obtained by subsequent dehydrobromination of the addition products.

7 Claims, No Drawings

PROCESS FOR THE PRODUCTION OF BROMO SUBSTITUTED TETRAHYDROFURAN SULFONES

The present invention relates to a process for the manufacture of β-bromoalkylsulfones and β-bromoalkenylsulfones and their dehydrobromination products by addition reaction of sulfonic acid bromides with olefins or acetylenes in the presence of a hydroperoxide and, optionally, of metal salts, followed, where appropriate, by dehydrobromination of the addition products obtained.

Methods for the addition reaction of sulfonic acid halides with olefins have in principle been disclosed, e.g. in the review by Stacey et al, Org. Reactions 13, 150 (1963). According to investigations by Asscher et al., J. Chem. Soc. 1964 4962 and Truce et al., J. Org. Chem. 35, 4220 (1970), benzenesulfonic acid chloride and methanesulfonic acid chloride undergo addition reactions, for example with styrene, butene, butadiene and acrylonitrile, in the presence of copper chloride, triethylammonium chloride and acetonitrile at from 95° to 110° C, but below the said temperature range the reaction remains incomplete and gives poor yields. The analogous reaction with acetylenes is described by Y. Amiel in Tetrah. Letters 1971, 661 and J. Org. Chem. 36, 3691 (1971).

Goldwhite et al., (Tetrahedron 21, 2743 (1965)) disclose that methanesulfonyl chloride will react with 1-heptene, in the course of 15 hours, whilst exposed to UV radiation. If the same reaction is attempted in the presence of dibenzoyl peroxide, an addition reaction does not occur. In reactions with mono-, di- and trichloromethanesulfonyl chloride, chlorination occurs, with elimination of sulfur dioxide.

Holt et al. (J. Chem. Soc. C, 1971, 3611) disclose that the reaction of benzenesulfonyl chloride with cyclohexene in the presence of aluminum chloride gives chlorination products, and that an addition reaction does not occur. Tanimoto et al., J. synth. org. Chem. Japan 26, 361 (1968) describe, e.g., the reaction of p-toluenesulfonic acid chloride with vinyl chloride in the presence of aluminum chloride to give the corresponding dichloroethylsulfone. To obtain a yield of 47% it is necessary to add an equivalent amount of aluminum chloride. An addition reaction of benzenesulfonic acid chloride, e.g. with styrene or phenylacetylene, at above 90° C, without using UV light or aluminum chloride, is described by L. J. Zakharkin (Zh. Org. Khim. 9 (1973) 5, 891 – 95). These conditions are not generally applicable since sensitive olefins and acetylenes undergo side-reactions under these conditions.

I have now found a process for the manufacture of β-bromoalkylsulfones and β-bromoalkenylsulfones and, where appropriate, of their dehydrobromination products, by addition reaction of sulfonic acid bromides with olefins and acetylenes and subsequent dehydrobromination, wherein the addition reaction is carried out in the presence of hydrogen peroxide or an organic hydroperoxide and optionally in the presence of catalytic amounts of a metal salt of sub-group IIb or of a salt of gallium, indium or thallium, and the addition product obtained is dehydrobrominated by conventional methods.

The present invention provides a process by means of which the addition reaction of sulfonic acid bromides with olefins and acetylenes can be carried out under particularly mild conditions because of the surprising and unforeseeable effect of hydroperoxides and, optionally, metal salts. The method extensively used in the art, namely the addition reaction of sulfonic acid chlorides in the presence of copper chloride, triethylammonium chloride and acetonitrile at about 100° C, falls in the case of sensitive olefins and acetylenes, since these decompose or polymerize under the reaction conditions and the desired adduct is only formed in moderate yields, if at all. Thus, attempted addition reaction of benzenesulfonic acid chloride with 2,5-dihydrofuran under the stated conditions gives less than 20% yield of the adduct, whilst the addition reaction with methanesulfonic acid chloride only gives traces of product. In contrast, using the process of the invention, addition reaction of benzenesulfonic acid bromide or methanesulfonic acid bromide with 2,5-dihydrofuran in the presence of a hydroperoxide and of a metal salt of the stated type gives the adducts in 98% yield and 95% yield, respectively. The mild reaction conditions even permit the use of olefins and acetylenes with relatively reactive functional groups, e.g. hydroxyl groups, as starting compounds, whilst under more severe conditions these groups could react with sulfonic acid halides.

There are no limitations on the sulfonic acid bromides and olefins or acetylenes used as starting compounds for the reaction according to the invention. The starting compounds may carry a great variety of substituents without interfering with the reaction.

The reaction according to the invention, and the sulfonic acid bromides and olefins or acetylenes used, may be represented by the general formulae below; the starting compound of the formula II is an acetylene is $R^4$ and $R^5$ together represent a bond, and accordingly the end product of the formula III is an olefin if $R^4$ and $R^5$ together represent a bond.

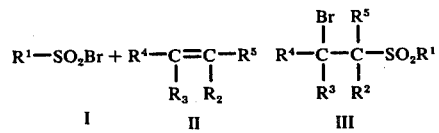

I    II    III

In the sulfonic acid bromides of the formula I, $R^1$ may be alkyl of 1 to 16 carbon atoms, such as methyl, ethyl, propyl, isopropyl, n-butyl, isobutyl, tert.-butyl, pentyl, heptyl, octyl, dodecyl or cetyl. Such alkyl radicals may have one or more substituents, e.g. halogen, especially chlorine, bromine and fluorine, alkoxy, especially methoxy ethoxy and propoxy, cyano, nitro, cycloalkyl of 3 to 8 carbon atoms in the ring, and phenyl, both of which may in turn be substituted. Examples of substituted alkyl are chloromethyl, trichloromethyl, 2-bromoethyl, 2-ethoxyethyl, 3-cyanopropyl, cyclohexylmethyl, β-cyclohexylethyl and 1-phenyl-substituted alkyl, especially phenylalkyl of 7 to 10 carbon atoms, wherein phenyl may be substituted by one or more radicals such as halogen, alkyl, nitro or alkoxy, e.g. benzyl, p-chlorobenzyl, p-methylbenzyl, p-nitrobenzyl, m-chlorobenzyl, m-nitrobenzyl, m-methoxybenzyl, o-chlorobenzyl, 2,4-dichlorobenzyl, 2-phenylethyl and 2-p-nitrophenylethyl.

$R^1$ may also be cycloalkyl of 3 to 8 carbon atoms in the ring, or a mononuclear or polynuclear cabocyclic aromatic radical which may be substituted by one or more of the following substituents: alkyl, alkoxy, trifluoromethyl, chlorine, bromine, fluorine, nitro or bromosulfonyl.

Specific examples of cycloalkyl and aromatic radicals are cyclopentyl, cyclohexyl, phenyl, p-methylphenyl, p-chlorophenyl, p-bromophenyl, p-nitrophenyl, p-methoxyphenyl, m-carboxyphenyl, m-nitrophenyl, m-bromosulfonylphenyl, m-methylphenyl, m-chlorophenyl, m-bromophenyl, m-trifluoromethylphenyl, o-chlorophenyl, o-methylphenyl, o-bromophenyl, 2,3-, 2,4-, 2,5-, 3,4- and 3,5-dimethylphenyl, 3,4-dimethoxyphenyl, p-diphenyl, 1-naphthyl, 2-naphthyl, 1-anthracenyl and 2-anthracenyl.

The preferred sulfonic acid bromides of the formula I are alkylsulfonic acid bromides and phenylsulfonic acid bromides; in the former, alkyl is of 1 to 5 carbon atoms, optionally substituted by halogen, especially fluorine, chlorine and bromide, and by alkoxy of 1 to 4 carbon atoms in the alkyl, preferably methoxy; in the phenylsulfonic acid bromides, phenyl is optionally monosubstituted or disubstituted by nitro, halogen, especially chlorine and bromine, alkoxy of 1 to 4 carbon atoms, preferably methoxy and ethoxy, or alkyl of 1 to 3 carbon atoms, preferably methyl.

The sulfonic acid bromides are known compounds or may be prepared, e.g., in accordance with methods described in the literature, e.g. by Ziegler and Spraque, J. Org. Chem. 16, 621 (1951) or Poshkus et al., J. Org. Chem. 28, 2766 (1963).

In the compounds of the formula II, $R^2$, $R^3$, $R^4$ and $R^5$ may be identical or different and are hydrogen, alkyl of 1 to 20 carbon atoms which may be substituted or unsubstituted, alkenyl of 1 to 20 carbon atoms, cycloalkyl of 3 to 8 carbon atoms in the ring, aryl, especially phenyl, halogen, especially fluorine, chlorine and bromine, nitrile or alkoxycarbonyl, acyl, alkoxy and acyloxy, each of up to 6 carbon atoms.

Furthermore, two substituents in a compound of the formula II may be linked to form a homocyclic or heterocyclic, monocyclic or polycyclic ring system of 3 to 16 ring members and up to 3 heteroatoms, and the olefinic bond may be endocyclic if $R^2$ and $R^3$ or $R^4$ and $R^5$ are linked to one another, or exocyclic if two radicals linked via a carbon atom are also linked to one another, e.g. $R^3$ with $R^4$ or $R^2$ with $R^5$.

Possible substituents of the alkyl radicals are halogen, especially fluorine, bromine and chlorine, nitrile, nitro and hydroxyl, and alkoxycarbonyl, acyl, alkoxy and acyloxy each of up to 6 carbon atoms, such as methoxycarbonyl, ethoxycarbonyl, n-butoxycarbonyl, formyl, acetyl, butyryl, methoxy, ethoxy, n-hexyloxy, acetoxy and propionoxy.

The preferred compounds of the formula II are olefins in which $R^4$ and $R^5$ are hydrogen and $R^2$ and $R^3$ have the above meanings.

Particularly preferred meanings of $R^2$ and $R^3$ are hydrogen, alkyl of 1 to 8 carbon atoms which is optionally monosubstituted or disubstituted by halogen, especially fluorine, chlorine and bromine, alkoxy of 1 to 4 carbon atoms, especially methoxy and ethoxy, hydroxyl, alkoxycarbonyl of 1 to 4 carbon atoms in the alkyl, nitrile, acyl and acyloxy each of 2 to 4 carbon atoms, and phenyl which is optionally monosubstituted or disubstituted by halogen, e.g., fluorine, chlorine or bromine, preferably chlorine, alkyl of 1 to 4 carbon atoms, especially methyl, alkoxycarbonyl of 1 to 4 carbon atoms in the alkyl, alkoxy of 1 to 4 carbon atoms and acyloxy of 2 to 4 carbon atoms.

In the preferred compounds, $R^2$ and $R^3$ together with the carbon atoms by which they are linked may form a 4-membered to 8-membered ring, which may optionally contain 1 or 2 hetero-atoms, especially oxygen and/or sulfur, and may be substituted by one or two alkyl radicals of 1 to 3 carbon atoms or alkoxy radicals of 1 to 3 carbon atoms.

Where $R^4$ and $R^5$ together represent a bond, the preferred meanings of $R^2$ and $R^3$ are again those singled out above, with the exception of the cyclic compounds.

Specific examples of olefins of the formula II are: 2-butene, 1-pentene, 1-octene, isobutene, 3,3-dimethyl-1-butene, 3-hexene, 1-decene, 1-dodecene, 1-hexadecene, 1-octadecene, vinyl chloride, 1,1-dichloroethylene, acrylonitrile, acrylic acid methyl ester, crotonic acid methyl ester, vinyl methyl ketone, vinyl ethyl ether, isobutenyl ethyl ether, propionic acid vinyl ester, 3-hydroxy-1-butene, 1,4-dihydroxy-2-butene, 1,4-diacetoxy-2-butene, 1,3-butadiene, 2,5-dimethyl-2,4-hexadiene, 1,4-dimethoxy-2-butene, 2-methyl-hept-2-en-6-one, isoprene, 1,9-decadiene, 1,4-octadiene, piperylene, vinylacetic acid, allyl cyanide, methylenecyclohexane, vinylcyclohexane, allylcyclohexane, ethylidenecyclopentane and styrene, p-chlorostyrene, p-bromostyrene, p-methylstyrene, m-nitrostyrene, 2,4-dimethylstyrene, α-methylstyrene, propenylbenzene, allylbenzene, methallylbenzene, 1,1-diphenylethylene, 2-vinylnaphthalene, 1-phenyl-2-butene, 2-phenylallyl chloride, cyclopentene, cyclohexene, 3-methylcyclohexene, 4-methylcyclohexene, 1-phenylcyclohexene, 3-methoxycyclohexene, cyclododecene, 3-cyclohexene-1-carboxyaldehyde, 2-cyclopentenylacetic acid, indene, acenaphthylene, norbornene, norbornadiene, 1,3-cyclohexadiene, 1,4-cyclohexadiene, cycloheptene, cycloheptatriene, cyclooctene, 1,3-cyclooctadiene, 1,5-cyclooctadiene, 2,5-dihydrofuran, 2,5-dimethoxy-2,5-dihydrofuran, 2-methyl-2,5-dihydrofuran, Δ-2-dihydropyran, 2,5-dihydrothiophene dioxide, 4,7-dihydro-1,3-dioxepin and 2-isopropyl-4,7-dihydro-1,3-dioxepin.

Specific examples of acetylenes, in which $R^4$ and $R^5$ together are a chemical bond, are 1-hexyne, 3-hexyne, 1-octyne, ethynylcyclohexane, phenylacetylene, diphenylacetylene, phenyl ethynyl ketone, propiolic acid ethyl ester, propargylonitrile, propargyl alcohol, 1,4-dihydroxy-2-butyne, 1,4-dimethoxy-2-butyne and propargyl chloride.

The essential feature of the invention is the addition of hydrogen peroxide or of an organic hydroperoxide when carrying out the addition reaction of a sulfonic acid bromide of the formula I with an olefin or acetylene of the formula II.

The amount of hydroperoxide is suitably not less than 0.5 mole percent, based on the amount of sulfonic acid bromide employed. As a rule, from 0.5 to 20, preferably from 5 to 15, mole percent are used.

Examples of organic hydroperoxides are tert.-butyl hydroperoxide, cumene by hydroperoxide, indan hydroperoxide, 9-hydroperoxydecalin, α-hydroperoxytetralin, diethyl ether hydroperoxide and tetrahydrofuran hydroperoxide. In general, the organic hydroperoxides are used in the form of their solutions.

In a particularly preferred embodiment, the requisite amount of hydroperoxide can be produced directly in the reaction mixture by passing in air or oxygen, if the solvent used, a specific additive in the solution, or the compound to be converted, themselves readily form a hydroperoxide.

The hydroperoxide can be formed in situ before starting the actual reaction, or during the reaction. The conditions for producing the requisite amount of hydroperoxide can easily be established by a preliminary experiment. Cyclohexene hydroperoxide and dihydrofuran hydroperoxide are particularly suitable in this context. The use of hydrogen peroxide, of which the requisite amount is added to the reaction mixture as, e.g., an aqueous solution of from 30 to 50% strength, is also particularly advantageous.

In many cases it is only the addition of the hydroperoxide which initiates the addition reaction. In all cases, it increases the rate of reaction and produces an advantageous increase in yield. The effect of the hydroperoxides is surprising and was unforeseeable, since the same effect is not observed, under the mild reaction conditions used, if conventional, commonly employed free-radical starters, such as dibenzoyl peroxide, azoisobutyronitrile or acetylcyclohexyl-sulfonyl peroxide and bis-tert.-butylcylohexyl peroxide, which two latter compounds are labile even at room temperature, are added.

In a particularly preferred embodiment, the addition reaction of sulfonic acid bromides with olefins and acetylenes in the presence of a hydroperoxide is additionally facilitated by adding salts of metals of sub-group 2 of the Periodic Table or a salt of gallium, indium or thiallium. Preferably, the salts are added as a solution, or in an at least partially dissolved form, to the reaction mixture, and are employed in amounts of from 1 to 10 mole percent, based on the amount of sulfonic acid bromide employed.

Specific examples of salts are zinc chloride, zinc bromide, zinc iodide, zinc cyanide, zinc nitrate, zinc sulfate, zinc phosphate, zinc formate, zinc acetate, cadmium chloride, cadmium bromide, cadmium sulfate, cadmium phosphate, cadmium nitrate, cadmium acetate, mercury-I chloride, mercury-II chloride, mercury bromide, mercury cyanide, mercury acetate and mercury benzoate.

The advantageous effect of these salts is illustrated in Tables 1 and 2. These tables also show that other metal salts are inert, or reduce the yield.

A suitable method of carrying out the reaction according to the invention is to mix the starting compounds of the formula I and II (in an approximately equimolar ratio, or with one of the reactants in excess), the hydroperoxide and the metal salt, if appropriate in a solvent, and to maintain a suitable temperature range by cooling or heating.

When running large industrial batches, it is advantageous to control the rate of reaction by gradual addition of the sulfonic acid bromide to the mixture of olefin or acetylene, hydroperoxide or metal salt. The reaction can also readily be carried out continuously.

The reaction according to the invention may be carried out in the presence or absence of solvents. Examples of suitable solvents are aliphatic and cycloaliphatic ethers, e.g. diethyl ether, tetrahydrofuran, dioxane and 1,2-diethoxyethane, aliphatic and cycloaliphatic hydrocarbons, such as petroleum ether, gasoline, cyclohexane, aromatic hydrocarbons, e.g. benzene, toluene and chlorobenzene, halogenated aliphatic hydrocarbons, e.g. methylene chloride, chloroform and carbon tetrachloride, carbon disulfide, esters, especially ethyl acetate, ketones, especially acetone and diethyl ketone, acetonitrile, nitromethane, lower alcohols, e.g. ethanol or isopropanol, or water.

One of the reactants, preferably the olefin or the acetylene, used in excess, may also serve as the solvent.

The appropriate reaction temperature to be maintained depends on the reactivity of the starting compounds. Reactions can be carried out at temperatures as low as −50° C. Whilst reaction temperatures above +70° C are feasible, they are less suitable since they minimize the advantages of the process according to the invention over other processes. A temperature range of from +10° to +50° C, in which the reactions are complete in a few minutes or hours, is preferred. In general, an induction period is observed at the beginning of the reaction; this in most cases lasts only a few seconds or minutes, and in rare cases up to one hour.

The $\beta$-bromoalkylsulfones and $\beta$-bromoalkenylsulfones which may be obtained in a simple manner by the process according to the invention can be dehydrobrominated by conventional methods to give the alkenylsulfones and alkynylsulfones and, as is shown by the examples, this reaction takes place readily. It is thereby possible to prepare biologically active compounds, e.g. pharmaceuticals, plant protection agents and the like, or compounds which are starting materials for further syntheses of, e.g., pharmaceuticals or plant protection agents.

As is disclosed, e.g., by German Published Application 2,143,989, 3-methylsulfonyl-2,5-dihydrofuran, 2-methylsulfonyl-1,4-dimethoxy-but-2-ene, 5-methylsulfonyl-4,7-dihydro-1,3-dioxepin and 3-phenylsulfonyl-2,5-dihydrofuran may be used with advantage to synthesize vitamins, especially vitamin B 6.

EXAMPLE 1

1-Methylsulfonyl-2-bromo-cyclohexane

A mixture of 64 g (0.78 mole) of cyclohexene, 60 ml of ether, 5 g of zinc chloride and 3.5 of 50% strength hydrogen peroxide is heated at from 30° to 35° C. 10 g of methanesulfonic acid bromide are added and the start of the reaction, detectable from the exothermicity, is awaited; it occurs after about 20 minutes. 109 g of methanesulfonic acid bromide (making a total of 0.75 mole) are then added dropwise in the course of 15 minutes, whilst applying slight cooling to give a temperature of 35° C, and the mixture is stirred at the same temperature until the reaction has ended (which requires about 4 hours).

After cooling to room temperature, 100 ml of water are added to the mixture and the batch is extracted with twice 100 ml of methylene chloride. The extracts are dried over sodium sulfate and the solvent is then stripped off. This leaves 175 g (0.725 mole) of 1-methylsulfonyl-2-bromo-cyclohexane; $n_D^{20} = 1.535$. The residue crystallizes on standing; melting point 45° – 48° C; yield 96%.

Determination of C, H and S: $C_7H_{13}BrO_2S$ (241): Calculated: C 34.8, H 5.4, S 13.3; Found: C 35.0, H 5.9, S 13.2.

On boiling the bromosulfone with triethylamine in benzene under reflux for 10 hours, 1-methylsulfonyl-cyclohexene of melting point 52° C (when crystallized from benzene/petroleum ether) is obtained.

Determination of C, H and S: $C_7H_{12}O_2S$ (160): Calculated: C 52.5, H 7.5, S 20.0; Found: C 52.8, H 7.5, S 19.8.

EXAMPLE 2

1-n-Butylsulfonyl-2-bromo-cyclohexane

A little n-butanesulfonic acid bromide is added to a mixture of 13.9 g (0.17 mole) of cyclohexene, 15 ml of ether and 0.7 ml of 50% strength hydrogen peroxide at 35° C, the start of the reaction is awaited (which requires about 10 minutes) and the remainder of a total of 30.6 g (0.15 mole) of n-butanesulfonic acid bromide is then added dropwise at the same temperature, with slight cooling. After stirring for 4 hours at 35° C, the solution of the resulting 1-n-butylsulfonyl-2-bromo-cyclohexane is diluted with 130 ml of ether and 0.15 mole of potassium tert.-butylate is added in portions, at −40° C. The mixture is stirred for 1 hour at 20° C, neutralized by adding a little glacial acetic acid and washed with water. The ether phase is dried and freed from solvent and the residual 1-n-butylsulfonyl-cyclohexene is distilled.

Boiling point: 120° − 125° C at 0.08 mm Hg; $n_D^{20}$ = 1.496.

Determination of C, H and S: $C_{10}H_{18}O_2S$ (202): Calculated: C 59.5, H 8.9, S 15.8; Found: C 59.4, H 9.0, S 16.0.

EXAMPLE 3

1-Phenylsulfonyl-2-bromo-cyclohexane

A mixture of 64 g (0.78 mole) of cyclohexene, 60 ml of ether, 166 g (0.75 mole) of benzenesulfonic acid bromide, 5 g of zinc chloride and 3.5 ml of 50% strength hydrogen peroxide is heated at 30° C. The slightly exothermic reaction which commences after about 45 minutes is counteracted by cooling to keep the temperatures at 35° C. The reaction mixture is partitioned between methylene chloride and water. After stripping off the methylene chloride, 227 g (0.75 mole) of 1-phenylsulfonyl-2-bromo-cyclohexane of melting point 72° C remain after recrystallization from benzene/cyclohexane, the melting point is 74° − 75° C.

Determination of C, H and S: $C_{12}H_{15}BrO_2S$ (303): Calculated: C 47.6, H 5.0, S 10.5; Found: C 47.9, H 5.2, S 10.5.

On boiling the bromosulfone with triethylamine in benzene under reflux for 10 hours, 1-phenylsulfonyl-cyclohexene of melting point 52° C (after crystallization from ether/petroleum ether) is obtained.

Determination of C, H and S: $C_{12}H_{14}O_2S$ (222): Calculated: C 64.9, H 6.3, S 14.4; Found: C 65.1, H 6.4, S 14.2.

EXAMPLE 4

3-Methylsulfonyl-4-bromo-tetrahydrofuran 31.8 g (0.20 mole) of methanesulfonic acid bromide are added dropwise in the course of 15 minutes to a mixture of 15.4 g (0.22 mole) of 2,5-dihydrofuran (containing 6% of water), 1.3 g of zinc chloride and 1.1 ml of 50% strength hydrogen peroxide. The mixture is kept at 30° C by cooling and is stirred at 30° C for a further 4 hours. After adding 30 ml of water, the batch is extracted with methylene chloride. After stripping off the solvent, 43.9 g (0.19 mole) of oily 3-methylsulfonyl-4-bromo-tetrahydrofuran remain; $n_D^{20}$ = 1.529, boiling point 130° C at 0.1 mm Hg. The product solidifies on standing and may be recrystallized from ether; melting point 53° − 55° C. Dehydrobromination with triethylamine in benzene or with aqueous sodium hydroxide solution gives an almost quantitative yield of 3-methylsulfonyl-2,5-dihydrofuran of melting point 42° − 43° C (after crystallization from benzene/ ether).

The same yield is obtained when the addition reaction is carried out in solutions in carbon tetrachloride, benzene, ether, acetonitrile and water. In the latter case, the addition of zinc chloride is unnecessary.

EXAMPLE 5

3-Methylsulfonyl-4-bromo-tetrahydrofuran 40 mmoles of 2,5-dihydrofuran having a known content of dihydrofuran hydroperoxide, produced by passing air through the 2,5-dihydrofuran and determined titrimetrically, are mixed with 1 mmole of zinc chloride and then reacted, at 30° C, with 20 mmoles of methanesulfonic acid bromide, and the yield of 3-methylsulfonyl-4-bromo-tetrahydrofuran is determined as a function of the particular hydroperoxide content. The results are summarized in the diagram shown in the drawing. They indicate that in the present example a hydroperoxide content of at least 5 mole percent is required to achieve quantitative conversion.

EXAMPLE 6

3-Methylsulfonyl-4-bromo-tetrahydrofuran

The yield of 3-methylsulfonyl-4-bromo-tetrahydrofuran in the reaction of 100 mmoles of 2,5-dihydrofuran and 100 mmoles of methanesulfonic acid bromide at 30° C is determined as a function of the added hydroperoxide and added metal salt (the mixture being worked up after 4 hours in each case). The results are summarized in the Table:

TABLE 1

| Hydroperoxide | Metal salt | yield of adduct |
|---|---|---|
| 5 mmoles of tert.-butyl hydroperoxide | 5 mmoles of $ZnCl_2$ | 85 mmoles |
| 5 mmoles of dihydrofuran hydroperoxide | 5 mmoles of $ZnCl_2$ | 87 mmoles |
| 10 mmoles of $H_2O_2$ | 5 mmoles of $ZnCl_2$ | 86 mmoles |
| " | 5 mmoles of $ZnCl_2$ | 84 mmoles[+] |
| " | None | 16 mmoles |
| " | 20 mmoles of $ZnCl_2$ | 83 mmoles |
| " | 2 mmoles of $ZnCl_2$ | 85 mmoles |
| " | 5 mmoles of $ZnBr_2$ | 81 mmoles |
| " | 5 mmoles of $CdBr_2$ | 85 mmoles |
| " | 5 mmoles of $HgCl_2$ | 80 mmoles |
| " | 5 mmoles of $AlCl_3$ | 15 mmoles |
| " | 5 mmoles of $SnCl_4$ | 15 mmoles |
| " | 10 mmoles of $FeCl_2$ | 6 mmoles |
| " | 5 mmoles of $FeCl_3$ | <2 mmoles |
| " | 5 mmoles of $CuBr_2$ | <2 mmoles |

[+]Worked up after 2.5 hours at 50° C

EXAMPLE 7

3-Methylsulfonyl-4-bromo-tetrahydrofuran

The reaction of 3.6 g (50 mmoles) of 2,5-dihydrofuran, 4.0 g (25 mmoles) of methanesulfonic acid bromide, 0.3 ml of 50% strength hydrogen peroxide and 2.5 mmoles of one of the salts listed in Table 2, at 30° C, is followed by thin layer chromatography and the conversion of methanesulfonic acid bromide is determined as a function of the salt added.

TABLE 2

| Metal salt | Duration (hours) | Conversion of $CH_3SO_2Br$ (%) | Reaction mixture |
|---|---|---|---|
| $ZnCl_2$ | <0.5 | 100 | Colorless |
| $Zn(NO_3)_2 \cdot 6 H_2O$ | <0.5 | 100 | Colorless |
| $ZnSO_4 \cdot 7 H_2O$ | 3 | 100 | Colorless |
| Zn (acetate)$_2$ | <0.5 | 100 | Colorless |
| $Cd(NO_3)_2 \cdot 4 H_2O$ | <0.5 | 100 | Colorless |
| $Hg_2Cl_2$ | 0.5 | 100 | Colorless |
| $Hg(CN)_2$ | <0.5 | 100 | Colorless |
| Hg (acetate)$_2$ | <0.5 | 100 | Colorless |
| $GaCl_3$ | <0.5 | 100 | Light yellow |
| $MgCl_2 \cdot 6 H_2O$ | 6 | <10 | yellow |

TABLE 2-continued

| Metal salt | Duration (hours) | Conversion of $CH_3SO_2Br$ (%) | Reaction mixture |
|---|---|---|---|
| | 12 | 10 | Black, viscous |
| $BaBr_2 \cdot 2 H_2O$ | 6 | <10 | Brown |
| | 12 | 10 | Black, viscous |
| TlCl | 0.5 | 10 | Colorless |
| | 6 | about 50 | Dark brown |

EXAMPLE 8

3-Ethylsulfonyl-4-bromo-tetrahydrofuran 130 g (0.75 mole) of ethanesulfonyl bromide are added dropwise at from 30° to 35° C, whilst cooling, to a mixture of 70 g (1.0 mole) of 2,5-dihydrofuran, 5 g of zinc chloride and 3.2 ml of tert.-butyl hydroperoxide. When the strongly exothermic reaction has subsided, the mixture is stirred for a further 2 hours at 40° C, 300 ml of water are then added and the pH is adjusted to 11-12 by adding about 280 ml of 4 N sodium hydroxide solution, whilst cooling the mixture to 20° C; this results in dehydrobromination of the 3-ethylsulfonyl-4-bromotetrahydrofuran which has been formed. After 10 minutes, the mixture is acidified slightly (to pH 5) with half-strength concentrated hydrochloric acid and extracted with methylene chloride. The extract is dried, the solvent is stripped off and the residue is distilled; it boils at 109°–110° C/0.1 mm Hg. 68 g (0.42 mole) of 3-ethylsulfonyl-2,5-dihydrofuran are obtained.

Determination of C, H and S: $C_6H_{10}O_3S$ (162): Calculated: C 44.4, H 6.2, S 19.8; Found: C 44.6, H 6.0, S 20.0.

EXAMPLE 9

3-Chloromethylsulfonyl-4-bromo-tetrahydrofuran 19.3 g (0.1 mole) of chloromethanesulfonic acid bromide are added in the course of 10 minutes to a solution of 14 g (0.2 mole) of 2,5-dihydrofuran and 0.5 ml of tert.-butyl hydroperoxide in 30 ml of chloroform at −40° C. After 15 minutes, 16.5 ml of triethylamine, dissolved in 20 ml of chloroform, are added dropwise at the same temperature, so as to dehydrobrominate the 3-chloromethylsulfonyl-4-bromotetrahydrofuran which has been formed. The mixture is stirred for half an hour at 20° C, washed with water, dried and concentrated. The residue is repeatedly digested with ether and the ether extract is distilled; it boils at 115°–120° C/0.2 mm Hg. 4.8 g of 3-chloromethylsulfonyl-2,5-dihydrofuran are obtained.

Determination of C, H and S: $C_5H_7ClO_3S$ (182.5): Calculated: C 32.9, H 3.8, S 17.5; Found: C 33.1, H 4.0, S 17.4.

EXAMPLE 10

3-Phenylsulfonyl-4-bromo-tetrahydrofuran 22 g (0.1 mole) of benzenesulfonic acid bromide are added to a mixture of 28 g (0.4 mole) of 2,5-dihydrofuran, 0.6 g of zinc chloride and 1 ml of tert.-butyl hydroperoxide at 25° C. The reaction temperature is kept below 35° C by cooling. After 6 hours, the mixture is partitioned between water and methylene chloride. The methylene chloride phase is dried and the solvent is stripped off in vacuo. An oily residue of 28.5 g (98 mmoles) of 3-phenylsulfonyl-4-bromo-tetrahydrofuran remains.

Determination of C, H and S: $C_{10}H_{11}BrO_3S$ (291): Calculated: C 41.2, H 3.8, S 11.0; Found: C 41.5, H 4.1, S 11.0.

Dehydrobromination of the adduct with aqueous sodium hydroxide solution or with triethylamine in benzene gives 3-phenylsulfonyl-2,5-dihydrofuran of melting point 68° – 69° C (after recrystallization from ether).

Determination of C and H: $C_{10}H_{10}O_3S$ (210): Calculated: C 57.2, H 4.8; Found: C 57.5, H 5.1.

EXAMPLE 11

3-(p-Nitrophenylsulfonyl)-4-bromo-tetrahydrofuran 9.8 g (37 mmoles) of p-nitrobenzenesulfonic acid bromide are added to a mixture of 10.5 g (150 mmoles) of 2,5-dihydrofuran, 250 mg of zinc chloride and 0.3 ml of tert.-butyl hydroperoxide at 25° C; a slightly exothermic reaction ensues. After 5 hours the precipitate is filtered off and dried in a high vacuum. 9.5 g (28 mmoles) of 3-(p-nitrophenylsulfonyl)-4-bromo-tetrahydrofuran are obtained, melting at 155° – 157° C after recrystallization from a mixture of benzene and petroleum ether.

Determination of C, H and S: $C_{10}H_{10}BrNO_5S$ (336): Calculated: C 35.8, H 3.0, S 9.5; Found: C 36.0, H 3.3, S 9.6.

The dehydrobromination of the adduct with triethylamine in benzene gives 3-(p-nitrophenylsulfonyl)-2,5-dihydrofuran of melting point 149° – 150° C (after recrystallization from ethyl acetate).

Determination of C, H and S: $C_{10}H_9NO_5S$ (255): Calculated: C 47.0, H 3.5, S 12.5; Found: C 47.3, H 3.8, S 12.7.

EXAMPLE 12

1-Methylsulfonyl-2-bromo-2-phenylethane 130 mg of zinc chloride, 3.2 g (20 mmoles) of methanesulfonic acid bromide and 0.15 ml of 50% strength hydrogen peroxide are successively added to a solution of 2.1 g (20 mmoles) of styrene in 5 ml of nitromethane. After 50 hours at room temperature, the mixture is taken up in methylene chloride and the solution is washed with water. The crude 1-methylsulfonyl-2-bromo-2-phenylethane which remains after stripping off the methylene chloride is dissolved in 10 ml of benzene and dehydrobrominated by adding 25 mmoles of triethylamine. Distillation at from 121° to 124° C at 0.01 mm Hg gives β-methylsulfonylstyrene, of melting point 77° – 79° C (after recrystallization from ether). According to the NMR spectrum (J = 15.5 Hz), the product is in the trans-configuration.

Determination of C, H and S: $C_9H_{10}O_2S$ (182): Calculated: C 59.4, H 5.5, S 17.6; Found: C 59.6, H 6.0, S 17.8.

EXAMPLE 13

2-Methylsulfonyl-3-bromo-1,4-dimethoxy-butane 32 g (0.2 mole) of methanesulfonic acid bromide are added to a mixture of 25.5 g (0.22 mole) of cis-1,4-dimethoxy-2-butene, 1.3 g of zinc chloride and 1.6 ml of 50% strength hydrogen peroxide; a slightly exothermic reaction ensues. After 3 hours at 35° C, and standing overnight at room temperature, the mixture is taken up in methylene chloride and the solution is washed with water. After stripping off the solvent, 55.0 g (0.2 mole) of 2-methylsulfonyl-3-bromo-1,4-dimethoxybutane of melting point 90° – 97° C remain.

Determination of C and H: $C_7H_{15}BrO_4S$ (275): Calculated: C 30.5, H 5.5; Found: C 30.8, H 5.4.

Dehydrobromination with triethylamine in benzene gives 2-methylsulfonyl-1,4-dimethoxy-2-butene, of boiling point 97° – 102° C at 0.1 mm Hg which, according to the NMR spectrum, is a mixture of 60% of the cis-compound and 40% of the trans-compound.

Determination of C, H and S: $C_7H_{14}O_4S$ (194): Calculated: C 43.3, H 7.3, S 16.5; Found: C 43.3, H 7.5, S 16.1.

EXAMPLE 14

2-Methylsulfonyl-3-bromo-1,4-dimethoxy-butane

A mixture of 2.3 g (20 mmoles) of trans-1,4-dimethoxy-2-butene, 130 mg of zinc chloride, 0.15 ml of 50% strength hydrogen peroxide and 3.2 g (20 mmoles) of methanesulfonic acid bromide is left to stand for 18 hours at room temperature. It is then taken up in methylene chloride, the solution is washed with water and dried and the solvent is stripped off again. 5.3 g (19 mmoles) of 2-methylsulfonyl-3-bromo-1,4-dimethoxybutane are obtained; this compound, and the 2-methylsulfonyl-1,4-dimethoxy-2-butene obtainable by dehydrobromination, are identical is spectroscopic properties to the products described in Example 13.

EXAMPLE 15

2-Bromo-3-methylsulfonyl-butyric acid methyl ester

A mixture of 2.0 g (20 mmoles) of crotonic acid methyl ester, 130 mg of zinc chloride, 0.1 ml of tert.-butyl hydroperoxide and 3.2 g (20 mmoles) of methanesulfonic acid bromide is heated at 50° C for 5 hours. The 2-bromo-3-methylsulfonylbutyric acid methyl ester formed is separated from unconverted starting compounds by fractional distillation; its boiling point is 95° – 105° C at 0.4 mm Hg.

The subsequent dehydrobromination with triethylamine in benzene gives 3-methylsulfonylcrotonic acid methyl ester as a mixture of the cis-isomer and trans-isomer in the ratio of 3:1.

EXAMPLE 16

1-Bromo-2-phenylsulfonyl-isobutyl ethyl ether

A mixture of 4.4 g (44 mmoles) of isobutenyl ethyl ether and 0.2 ml of tert.-butyl hydroperoxide is added dropwise in the course of 15 minutes, at from 5° to 10° C, to 8.8 g (40 mmoles) of benzenesulfonic acid bromide. An exothermic reaction ensues and the unstable adduct, 1-bromo-2-phenylsulfonyl-isobutyl ethyl ether, is formed; this undergoes a strongly exothermic secondary reaction in the course of 1 hour at room temperature. Recrystallization of the product mixture from a mixture of benzene and petroleum ether gives 2-phenylsulfonyl-isobutyraldehyde of melting point 103° – 104° C.

Determination of C, H and S: $C_{10}H_{12}O_3S$ (212.3): Calculated: C 56.6, H 5.6, S 15.1; Found: C 56.8, H 5.3, S 15.1.

EXAMPLE 17

1-Methylsulfonyl-2-bromo-3-ol 64 g (0.4 mole) of methylsulfonic acid bromide are added dropwise in the course of 15 minutes, at about 30° C, to a mixture of 31.7 g (0.44 mole) of but-1-en-3-ol, 2.6 g of zinc chloride and 3 ml of 50% strength hydrogen peroxide. After 2 hours, the mixture is taken up in methylene chloride and the solution is washed with water. After stripping off the solvent, 86.3 g (0.37 mole) of 1-methylsulfonyl-2-bromo-butan-3-ol remain.

Determination of C, H and S: $C_5H_{11}BrO_3S$ (231): Calculated: C 26.0, H 4.8, S 13.8; Found: C 26.3, H 5.0, S 13.9.

Dehydrobromination with triethylamine in benzene at room temperature gives 1methylsulfonyl-but-1en-3-ol which melts at 70° – 72° C after recrystallization from a mixture of ethyl acetate and petroleum ether; according to the NMR spectrum, the compond has the trans-configuration; J = 15.5 Hz.

Determination of C, H and S: $C_5H_{10}O_3S$ (150): Calculated: C 40.0, H 6.7, S 21.3; Found: C 39.8, H 6.9, S 21.1.

EXAMPLE 18

1-Methylsulfonyl-2-bromo-cyclopentane 32 g (0.2 mole) of methanesulfonic acid bromide are added dropwise to a mixture of 17 g (0.25 mole) of cyclopentene, 25 ml of ether, 1.25 ml of tert.-butyl hydroperoxide and 1.25 g of zinc chloride and the temperature is kept at 40° C by cooling; the induction period is about 5 minutes. After stirring for 2 hours at room temperature, the 1-methylsulfonyl-2-bromo-cyclopentane formed is dehydrobrominated by adding potassium tert.-butylate in tetrahydrofuran at −50° C. After distillation, 21.9 g (0.15 mole) of 1-methylsulfonyl-cyclopentene of boiling point 90° C at 0.05 mm Hg and melting point 50° – 52° C are obtained.

Determination of C, H and S: $C_6H_{10}O_2S$ (146): Calculated: C 49.3, H 6.9, S 21.9; Found: C 49.5, H 7.0, S 21.5.

EXAMPLE 19

1-Methylsulfonyl-2-bromo-3-methyl-cyclohexane 20.6 g (130 mmoles) of methanesulfonic acid bromide are added dropwise at 40° C to a mixture of 14.6 g (150 mmoles) of 3-methylcyclohexene, 15 ml of ether, 0.75 ml of tert.-butyl hydroperoxide and 0.7 g of zinc chloride; the induction period is about 10 minutes. The mixture is stirred for a further hour at 45° C and the 1-methylsulfonyl2-bromo-3-methyl-cyclohexane which has been formed is then hydrobrominated by adding potassium tert.-butylate at −40° C. The reaction product 1-methylsulfonyl-3-methyl-1-cyclohexene, after purification by distillation, contains — according to the NMR spectrum — small proportions of 1-methylsulfonyl-6-methyl-1-cyclohexene. Boiling point 114° – 118° C at 0.1 mm Hg; $n_D^{20}$ 1.501.

Determination of C and H: $C_8H_{14}O_2S$ (174): Calculated: C 55.1, H 8.0; Found: C 54.8, H 8.0.

EXAMPLE 20

1-Methylsulfonyl-2-bromo-4 and -5-methylcyclohexane 15.9 g (100 mmoles) of methanesulfonic acid bromide are added dropwise at 40° C to a mixture of 10.5 g (110 mmoles) of 4-methylcyclohexene, 10 ml of ether, 0.5 g of zinc chloride and 0.5 ml of tert.-butyl hydroperoxide; the induction period is about 5 minutes. After stirring for a further 30 minutes at 40° C, the adduct mixture formed, which contains 1-methylsulfonyl-2-bromo-4-methyl-cyclohexane and 1-methylsulfonyl-2-bromo-5-methyl-cyclohexane, is dehydrobrominated by adding potassium tert.-butyl at −40° C. Fractional distillation gives 15.2 g (87 mmoles) of a mixture of 1-methylsulfonyl-4-methylcyclohexene and 1-methylsulfonyl-5-methyl-cyclohexene of boiling point 105° – 106° C at 0.05 mm Hg; $n_D^{20}$ 1.498.

Determination of C and H: $C_8H_{14}O_2S$ (174): Calculated: C 55.1, H 8.0; Found: C 55.4, H 7.9.

EXAMPLE 21

1-Phenylsulfonyl-2-bromo-4- and -5-methyl-cyclohexane 17.7 g (80 mmoles) of benzenesulfonic acid bromide are added dropwise at from 40° to 45° C to a mixture of 8.3 g (88 mmoles) of 4-methyl-cyclohexene, 10 ml of ether, 0.5 g of zinc chloride and 0.5 ml of tert.-butyl hydroperoxide. After stirring for 4 hours at room temperature, the adduct mixture formed, which contains 1-phenylsulfonyl-2-bromo-4-methyl-cyclohexane and 1-phenylsulfonyl-2-bromo-5-methylcyclohexane, is dehydrobrominated by adding potassium tert.-butylate at −50° C. 16.2 g (68 mmoles) of a mixture of 1-phenylsulfonyl-4-methyl-1-cyclohexene and 1-phenylsulfonyl-5-methyl-1-cyclohexene, of $n_D^{20}$ = 1.551, are obtained.

Determination of C, H and S: $C_{13}H_{16}O_2S$ (236): Calculated: C 66.2, H 6.8, S 13.5; Found: C 66.5, H 6.8, S 13.2.

EXAMPLE 22

2-Phenylsulfonyl-3-bromo-norbornane 22 g (100 mmoles) of benzenesulfonic acid bromide are added dropwise, with slight cooling, to a mixture of 10.3 g (110 mmoles) of norbornene, 30 ml of acetonitrile, 0.6 g of zinc chloride and 0.5 ml of tert.-butyl hydroperoxide at from 25° to 30° C. After standing for 24 hours at room temperature, the reaction mixture is taken up in methylene chloride and washed with water. After stripping off the solvent, 30.8 g (98 mmoles) of 2-phenylsulfonyl-3-bromo-norbornane are left as a mixture of the exo-exo-isomer and exo-endo-isomer, of melting point 108° – 110° C.

Determination of C, H and S: $C_{13}H_{15}BrO_2S$ (315): Calculated: C 49.5, H 4.8, S 10.1; Found: C 49.3, H 4.9, S 10.1.

The isomers can be separated by fractional crystallization from a mixture of chloroform and cyclohexane.

EXAMPLE 23

1-Methylsulfonyl-2-bromo-cycloheptane 40 g (0.25 mole) of methanesulfonic acid bromide are added dropwise at 45° C to a mixture of 26.8 g (0.28 mole) of cycloheptene, 20 ml of ether, 1.9 of zinc chloride and 1.2 ml of 50% strength hydrogen peroxide. After the strongly exothermic reaction has subsided, the reaction mixture is heated at 50° C for 1 hour, and then taken up in methylene chloride. The solution is washed with water, the solvent is stripped off and the residue, 1-methylsulfonyl-2-bromocycloheptane, is recrystallized from a mixture of benzene and cyclohexane; melting point 87° – 89° C.

Determination of C, H and S: $C_8H_{15}BrO_2S$ (255): Calculated: C 37.6, H 5.9, S 12.5; Found: C 37.7 H 5.9, S 12.5.

Dehydrobromination of the product with triethylamine in boiling benzene gives 1-methylsulfonyl-cycloheptene, of boiling point 118° – 120° C at 0.1 mm Hg, which is crystalline at room temperature.

Determination of C and H: $C_8H_{14}O_2S$ (174); Calculated: C 55.1, H 8.1; Found: C 55.1, H 8.3.

EXAMPLE 24

α-Bromo-β-phenylsulfonyl-styrene

A mixture of 22.44 g (0.22 mole) of phenylacetylene, 50 ml of acetonitrile, 44 g (0.2 mole) of benzenesulfonic acid bromide, 1 ml of tert.-butyl hydroperoxide and 1.3 g of zinc chloride is stirred for 4 hours at from 30° to 35° C. The acetonitrile is then stripped off, the residue is taken up in methylene chloride and the solution is washed with water. After distilling off the methylene chloride, 63 g (0.195 mole) of crystalline α-bromo-β-phenylsulfonyl-styrene are left. This material is recrystallized from a mixture of ether and petroleum ether and then has a melting point of 84° – 85° C.

Dehydrobromination of the product with triethylamine in benzene at room temperature gives phenylethynyl-phenylsulfone, of melting point 73° C after recrystallization from a mixture of ether and petroleum ether.

Determination of C, H and S: $C_{14}H_{10}O_2S$ (242): Calculated: C 69.5, H 4.1, S 13.2; Found: C 69.2, H 4.3, S 13.0.

EXAMPLE 25

2-Methylsulfonyl-3-bromo-1,4-dimethoxy-2-butene 32 g (0.2 mole) of methanesulfonic acid bromide are added dropwise in the course of 15 minutes at 35° C, whilst cooling, to a mixture of 25.1 g (0.22 mole) of 1,4-dimethoxy-2-butyne, 1.3 g of zinc chloride and 1 ml of tert.-butyl hydroperoxide. After 1.5 hours, the reaction mixture is taken up in methylene chloride and the solution is washed with water. After stripping off the solvent, the residue is subjected to fractional distillation; the product has a boiling point of 115° – 116° C at 0.25 mm Hg.

Determination of C, H and Br: $C_7H_{13}BrO_4S$ (273): Calculated: C 30.8, H 4.8, Br 29.3; Found: C 31.0, H 5.0, Br 29.1.

EXAMPLE 26

1-Phenylsulfonyl-2-bromo-3-chloro-1-propene 44 g (0.2 mole) of benzenesulfonic acid bromide are added dropwise at 35° C, whilst cooling, to a mixture of 17.9 g (0.24 mole) of propargyl chloride, 1.0 ml of tert.-butyl hydroperoxide and 1.3 g of zinc chloride. The constituents which are volatile below 90° C at 0.2 mm Hg are distilled off and the residue is purified by column chromatography over silica gel (using a 1:1 mixture of methylene chloride and petroleum ether). The eluate is recrystallized from cyclohexane and then has a melting point of 70° – 73° C; according to the NMR spectrum, the product is a mixture of the cis-isomer and trans-isomer.

Determination of C, H and S: $C_9H_8BrClO_2S$ (295.5): Calculated: C 36.6, H 2.7, S 10.8; Found: C 36.7, H 3.0, S 10.6.

EXAMPLE 27

1-Methylsulfonyl-2-bromo-octane 16 g (0.1 mole) of methanesulfonic acid bromide are added dropwise at 50° C to a mixture of 16.8 g (0.15 mole) of 1-octene, 0.7 g of zinc chloride and 0.5 ml of tert.-butyl hydroperoxide. The strongly exothermic reaction, which is moderated by cooling, is complete after 15 minutes. The mixture is taken up in 50 ml of chloroform and the chloroform solution is washed twice with water, dried over sodium sulfate and concentrated. Distillation of the residue gives 25.1 g of 1-methylsulfonyl-2-bromo-octane of boiling point 133° C at 0.25 mm Hg; $n_D^{20}$ 1.4903.

Determination of C, H and S: $C_9H_{19}BrO_2S$ (271): Calculated: C 39.8, H 7.0, S 11.8; Found: C 40.0, H 7.3, S 11.5.

7.5 g (60 mmoles) of potassium tert.-butylate are added to a solution of 13.6 g (50 mmoles) of 1-methylsulfonyl-2-bromo-octane in 50 ml of ether at $-25°$ C. The mixture is warmed to 0° C and then washed with water. After stripping off the solvent, 9 g of 1-methylsulfonyl-1-octene, of $n_D^{25}$ = 1.488 remains; according to the NMR spectrum, the product is a 1:1 mixture of the cis-isomer and trans-isomer.

EXAMPLE 28

1-Methylsulfonyl-2-bromo-3-acetoxypropane 16 g (0.1 mole) of methanesulfonic acid bromide are added dropwise at 60° C to a mixture of 17.5 g (0.15 mole) of allyl acetate, 0.7 g of zinc chloride and 0.5 ml of tert.-butyl hydroperoxide. After an induction period of a few minutes the reaction is strongly exothermic and has to be kept at the temperature indicated by cooling. The mixture is taken up in 50 ml of chloroform and the chloroform solution is washed twice with water, dried over sodium sulfate and concentrated. There is obtained 24.5 g of 1-methylsulfonyl-2-bromo-3-acetoxypropane as a colorless oil; $n_D^{25}$ 1.498.

To dissolve the product in 120 ml of benzene 18 ml of triethylamine is added dropwise at 30° C. The mixture is stripped for another 45 minutes at 40° C, cooled with ice and washed three times, each time with 50 ml of water. After separation of the solvent and distillation of the residue there is obtained 1-methylsulfonyl-3-acetoxypropene as a cis/trans-isomer mixture (according to the NMR spectrum in a ratio of 1:2); $n_D^{25}$ 1.477.

Determination of C and H: $C_6H_{10}O_4S$ (178): Calculated: C 40.5, H 5.6; Found: C 40.4, H 5.8.

I claim:

1. A process for the manufacture of bromo-tetrahydrofurans which comprises subjecting a sulfonic acid bromide of the formula I $$R^1SO_2Br \qquad (I)$$

where $R^1$ is alkyl of 1–16 carbon atoms or alkyl of 1–16 carbon atoms substituted by fluorine, chlorine, bromine, methoxy, ethoxy, propoxy, cyano, nitro, cycloalkyl of 3–8 carbon atoms, phenyl, or phenyl substituted by chloro, methyl, nitro, or methoxy; or $R^1$ is cycloalkyl of 3–8 carbon atoms, m-carboxyphenyl, a mononuclear of polynuclear carbocyclic aromatic radical, or said aromatic radical substituted by methyl, methoxy, trifluoromethyl, chlorine, bromine, fluorine, nitro or bromosulfonyl, to an addition reaction at a temperature of 10° to 50° C with a substantially equal molar amount of an unsaturated compound of formula (II)

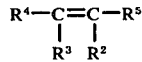

wherein $R^4$ and $R^5$ respectively are hydrogen and $R^2$ and $R^3$ together with the unsaturated carbon atoms to which they are linked in formula (II) represent a 2,5-dihydrofuran ring, or said ring substituted by one or two alkyl groups of 1–3 carbon atoms or by one or two alkoxy groups of 1–3 carbon atoms in the presence of hydrogen peroxide or an organic hydroperoxide in an amount of 0.5 to 20 mol percent, based on the amount of said sulfonic acid bromide employed, to produce a 3-sulfone-4-bromo-tetrahydrofuran compound in which the 3-sulfone group bears the radical $R^1$.

2. A process as claimed in claim 1 wherein the organic hydroperoxide is produced in situ by passing air or oxygen into the reaction mixture.

3. A process as claimed in claim 1 wherein said addition reaction is carried out in the presence of 1 to 10 mol percent, based on the sulfonic acid bromide, of a metal salt of subgroup 2 of the Periodic Table or a salt of gallium, indium or thallium.

4. A process as claimed in claim 1 wherein the addition reaction is carried out in the presence of 1 to 10 mol percent, based on said sulfonic acid bromide, of a salt selected from the group consisting of zinc chloride, zinc bromide, zinc iodide. zinc cyanide, zinc nitrate, zinc sulfate, zinc phosphate, zinc formate, zinc acetate, cadmium chloride, cadmium bromide, cadmium sulfate, cadmium phosphate, cadmium nitrate, cadmium acetate, mercury-I chloride, mercury-II chloride, mercury bromide, mercury cyanide, mercury acetate and mercury benzoate.

5. A process as claimed in claim 1 wherein $R^1$ is alkyl of 1 to 5 carbon atoms, alkyl of 1 to 5 carbon atoms substituted by fluorine, chlorine, bromine, or alkoxy of 1 to 4 carbon atoms, phenyl or phenyl which is mono-substituted or di-substituted by nitro, chlorine, bromine, alkoxy of 1 to 4 carbon atoms or alkyl of 1 to 3 carbon atoms.

6. A process as claimed in claim 5 wherein said unsaturated compound is 2,5-dihydrofuran.

7. A process as claimed in claim 1 wherein said unsaturated compound is 2,5-dihydrofuran.

* * * * *